(12) United States Patent
Schumaier

(10) Patent No.: US 11,122,378 B1
(45) Date of Patent: *Sep. 14, 2021

(54) HEARING AID DRYER AND DISINFECTION KIT

(71) Applicant: Daniel R. Schumaier, Elizabethton, TN (US)

(72) Inventor: Daniel R. Schumaier, Elizabethton, TN (US)

(*) Notice: Subject to any disclaimer, the term of this patent is extended or adjusted under 35 U.S.C. 154(b) by 100 days.

This patent is subject to a terminal disclaimer.

(21) Appl. No.: 16/532,868

(22) Filed: Aug. 6, 2019

(51) Int. Cl.
| A61L 2/10 | (2006.01) |
| H04R 25/00 | (2006.01) |
| A61L 2/00 | (2006.01) |
| F26B 3/00 | (2006.01) |
| F26B 19/00 | (2006.01) |

(52) U.S. Cl.
CPC ........... H04R 25/65 (2013.01); A61L 2/0047 (2013.01); F26B 3/00 (2013.01); F26B 19/00 (2013.01); *H04R 2460/17* (2013.01)

(58) Field of Classification Search
CPC . A61L 2/0047; A61L 2/10; A61L 2/24; A61L 2/26
See application file for complete search history.

(56) References Cited

U.S. PATENT DOCUMENTS

| 5,404,105 A | 4/1995 | Chari |
| 5,640,783 A | 6/1997 | Schumaier |
| 5,852,879 A | 12/1998 | Schumaier |
| D414,304 S | 9/1999 | Schumaier |
| D467,394 S | 12/2002 | Schumaier |
| 7,062,057 B2 | 6/2006 | Wu |
| D536,491 S | 2/2007 | Schumaier |
| 7,182,820 B2 | 2/2007 | Campbell et al. |
| 8,112,900 B2 | 2/2012 | Romanek |
| 9,709,327 B2 | 7/2017 | Marchiori |
| 9,843,870 B2 | 12/2017 | Naumann |
| 2004/0073275 A1 | 4/2004 | Maltan et al. |
| 2004/0258559 A1 | 12/2004 | Paskal et al. |
| 2006/0220620 A1 | 10/2006 | Aradachi et al. |
| 2009/0296968 A1 | 12/2009 | Wu et al. |
| 2010/0088916 A1 | 4/2010 | Romanek |
| 2012/0216418 A1 | 8/2012 | Serman et al. |
| 2013/0004367 A1 | 1/2013 | Roberts |
| 2013/0330235 A1* | 12/2013 | Stibich ............... A61L 2/24 422/105 |
| 2015/0162770 A1 | 6/2015 | Choi et al. |

(Continued)

FOREIGN PATENT DOCUMENTS

| CN | 201018665 | 2/2008 |
| CN | 103747388 A | 4/2014 |

(Continued)

*Primary Examiner* — Sean M Luck
(74) *Attorney, Agent, or Firm* — Luedeka Neely Group, P.C.

(57) ABSTRACT

A portable airtight electronic component dryer device including a container having an interior portion for receiving one or more electronic components for drying; a desiccant disposed in the interior portion of the container; and a removable lid for the container. The removable lid contains a disinfecting light source, and a power source for providing power to the disinfecting light source. Light generated by the disinfecting light source is directed into the interior portion of the container.

12 Claims, 4 Drawing Sheets

(56) References Cited

U.S. PATENT DOCUMENTS

| | | | |
|---|---|---|---|
| 2015/0174426 A1 | 6/2015 | Germain et al. | |
| 2016/0008498 A1* | 1/2016 | Boysset | B65D 81/18 422/23 |
| 2016/0074545 A1 | 3/2016 | Kim | |
| 2016/0101202 A1* | 4/2016 | Gil | A61L 2/10 422/186.3 |
| 2016/0165367 A1 | 6/2016 | Ochsenbein | |
| 2016/0277848 A1 | 9/2016 | Naumann | |
| 2016/0301287 A1 | 10/2016 | Nagata et al. | |
| 2017/0023299 A1 | 1/2017 | Leung et al. | |
| 2018/0123355 A1 | 5/2018 | Olson et al. | |
| 2018/0123367 A1 | 5/2018 | Higgins et al. | |
| 2019/0208342 A1 | 7/2019 | Higgins et al. | |
| 2020/0267483 A1* | 8/2020 | Schumaier | F26B 3/04 |

FOREIGN PATENT DOCUMENTS

| | | |
|---|---|---|
| CN | 203589776 U | 5/2014 |
| CN | 104534822 A | 4/2015 |
| CN | 205901402 U | 1/2017 |
| DE | 202017107151 U1 | 1/2018 |
| KR | 20060012144 A | 2/2006 |
| KR | 20120085980 A | 8/2012 |
| KR | 101466886 B1 | 12/2014 |
| WO | 2007066908 A1 | 6/2007 |

\* cited by examiner

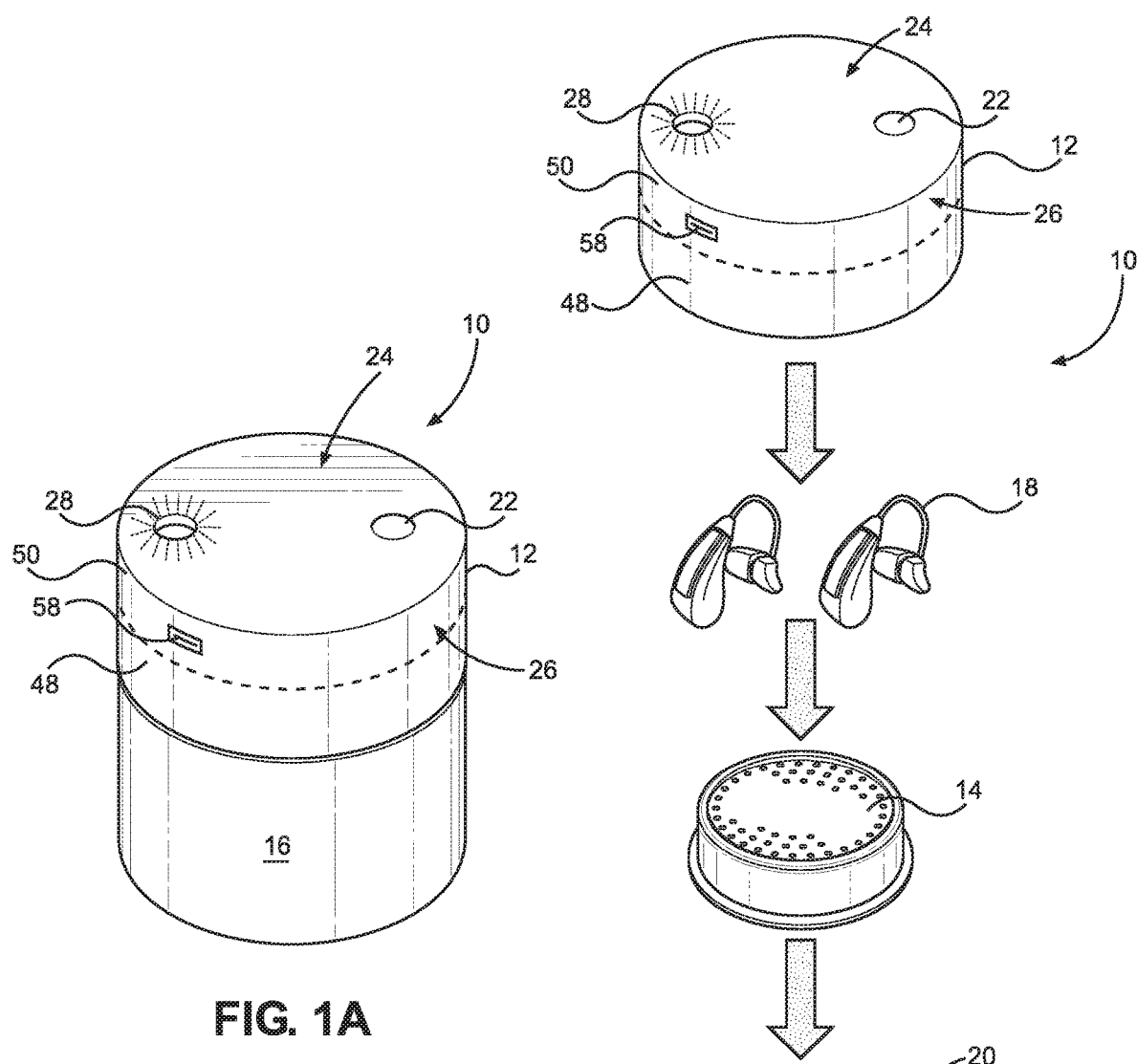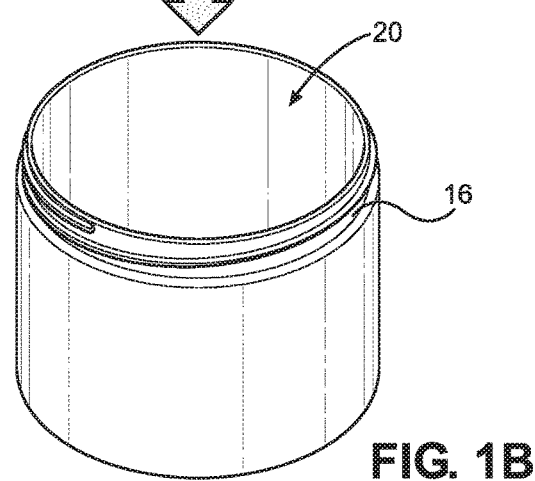
FIG. 1A
FIG. 1B

HEARING AID DRYER AND DISINFECTION KIT

TECHNICAL FIELD

The disclosure relates to a portable drying device for drying electronic and nonelectronic components, and in particular to a hearing aid drying and disinfection kit.

BACKGROUND AND SUMMARY

A hearing aid patient relies on a hearing aid device, and thus its components, to reliably function. Hearing aid devices comprise numerous sensitive electronic components that require periodic maintenance. These components may include a receiver, microphone, volume control, potentiometers, contacts, rechargeable batteries, and circuitry.

Hearing aid devices are subject to a moist environment when worn by a user. Moisture alone may negatively impact device performance and longevity particularly with regard to the electronic components. Moisture also aggravates the buildup of ear wax, dirt, and grime, which may also deteriorate performance and longevity.

Untreated moisture may, for example, cause corrosion on contacts, potentiometers, circuitry, batteries, and wires, condensation on screens or diaphragms in the microphone/receiver, and/or loss of sensitivity of or change in the frequency response of the microphone/receiver. Further, untreated moisture and buildup may lead to ear infections.

Reducing moisture content and/or facilitating the removal of buildup and bacteria, assists in the reliable functionality, maintainability, cleanliness, and longevity of hearing aid devices and prevents unwanted ear infections. Many hearing aid maintenance systems are rather large and expensive and may not be conveniently carried in a purse, suitcase, or brief-case. Accordingly, there is a need for a simple, relatively small, portable, battery-powered, and inexpensive hearing aid maintenance kit that reduces moisture and disinfects the hearing aids.

In view of the foregoing, an embodiment of the disclosure provides an electronic component dryer device including a container having an interior portion for receiving one or more electronic components for drying, a desiccant disposed in the interior portion of the container, and a removable lid for the container. The removable lid contains a disinfecting light source, and a power source for providing power to the disinfecting light source. Light generated by the disinfecting light source is directed into the interior portion of the container.

In another embodiment there is provided an improved electronic component dryer kit that includes an air-tight container and a removable desiccant. The improvement includes a removable lid for the container, wherein the removable lid contains a disinfecting light source, and a power source for providing power to the disinfecting light source. The light generated by the disinfecting light source is directed into the interior portion of the container.

In some embodiments, the removable lid includes a timer circuit that is isolated from the interior portion of the container, wherein the timer circuit controls the disinfecting light source to operate for a predetermined period of time. In other embodiments, the predetermined period of time can be controlled by firmware in the processor to range from minutes to hours.

In some embodiments, wherein the removable lid also includes a switch that is isolated from the interior portion of the container for activating the disinfecting light source. In other embodiments, the switch comprises a capacitive switch. In still other embodiments, the capacitive switch is on a top portion of the removable lid.

In some embodiments, the disinfecting light source comprises an ultraviolet light source. In other embodiments, the ultraviolet light source includes one more ultraviolet light emitting diodes or one or more ultraviolet lamps.

In some embodiments, the removable lid also includes a power on/off indicator.

In some embodiments, the removable lid is an air-tight removable lid.

In some embodiments, the desiccant is a replaceable desiccant holder containing desiccant and having vent holes therein.

In some embodiments, the dryer device includes lid removal detection circuitry comprising a magnetic switch or metal contacts on the container and the lid that closes a circuit to provide power to the disinfecting light source when lid is secured to the container.

BRIEF DESCRIPTION OF THE DRAWINGS

The invention will be further understood from the drawings herein of certain preferred embodiments, wherein the structures are not drawn to scale, and the following description thereof, wherein:

FIG. 1A is a perspective view, not to scale, of a hearing aid dryer and disinfection kit according to the disclosure.

FIG. 1B is an exploded, perspective view, not to scale, of the hearing aid dryer and disinfection kit of FIG. 1A.

DESCRIPTION OF THE PREFERRED EMBODIMENTS

Figure 2A:
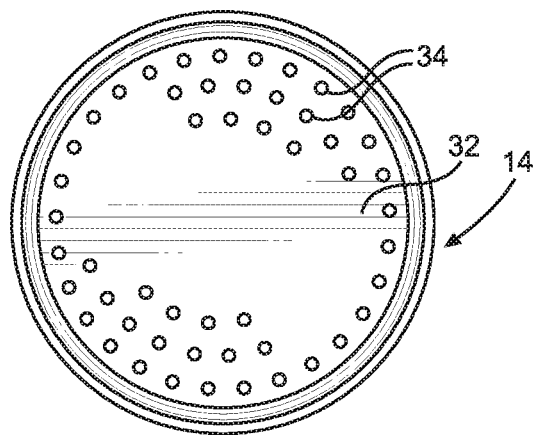
FIG. 2A is a plan, top view of a removable desiccant for the hearing aid dryer and disinfection kit according to FIG. 1A.

With reference to FIGS. 1A and 1B there are illustrated a perspective view and an exploded view, not to scale, of an electronic component dryer and disinfection device 10 showing the primary components thereof. In various embodiments, the device 10 may be used to dry and disinfect various types of electronic components, including but not limited to hearing aids, personal sound amplifiers, ear buds, and in-ear monitors. The device 10 includes a removable lid 12, a removable desiccant holder 14 containing desiccant, and a container 16 for holding hearing aids 18 to be dried and disinfected. An interior 20 of the container 16 is sized to contain the desiccant holder 14 and the hearing aids 18 during a drying and disinfection procedure. The disinfection procedure is initiated by a switch 22 on a top portion 24 or side portion 26 of the lid 12. During the disinfection procedure, an indicator lamp 28 attached to the lid 12, such as an LED lamp, may be illuminated to warn a user not to remove the lid 12 of the device 10 until the disinfection step is completed.

The lid 12, desiccant holder 14 and container 16 may have a cylindrical shape to facilitate a screw-on or snap-on lid 12. However, any other shaped container, lid and desiccant holder may be used including square or rectangular shaped lids, desiccant holders and containers. The lid 12 may also provide an air-tight seal when attached to the container 16 so that ambient moisture external to the device 10 is avoided. An O-ring type gasket may be included for the purpose of providing the air-tight seal.

Figure 2B:
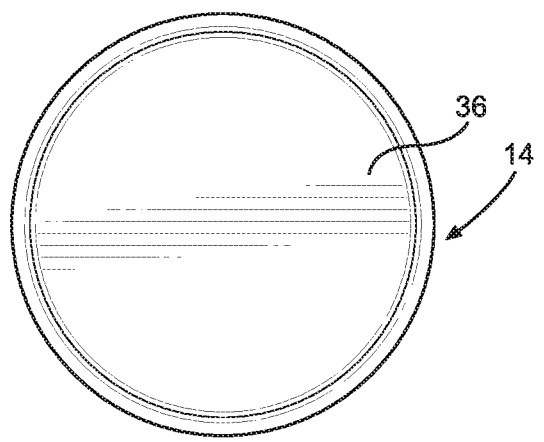
FIG. 2B is a plan, bottom view of a removable desiccant for the hearing aid dryer and disinfection kit according to FIG. 1A.

FIG. 2A is a top, plan view, of the desiccant holder 14 containing desiccant. The desiccant may include any moisture absorbing material such as supported granular CaO, CaCl2, ZnCl2, CUSO4, silica gel or the like. The amount of desiccant in the desiccant holder 14 may be sufficient to dry hearing aids for a month or more. A top side 32 of the desiccant holder 14 has a plurality of vent holes 34 therein for transferring moisture from the hearing aids 18 to desiccant in the desiccant holder 14. A bottom side 36 of the desiccant holder 14, as shown in FIG. 2B is devoid of vent holes.

Figure 3:
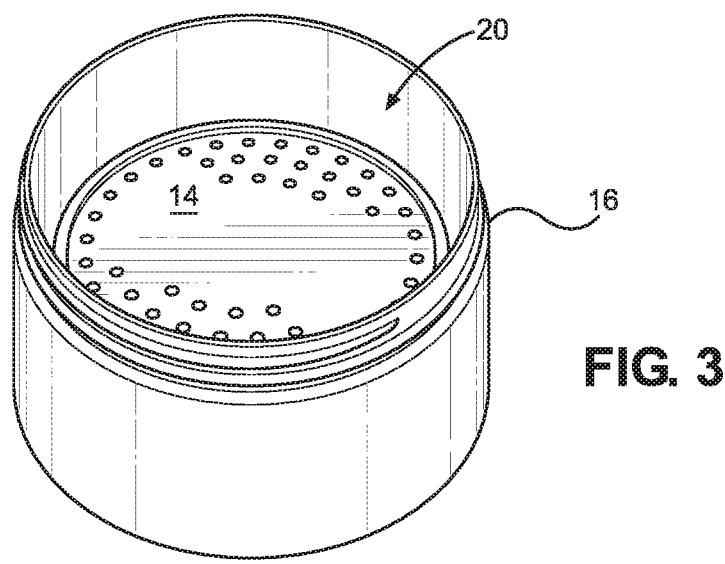
FIG. 3 is a perspective view of a container for the hearing aid dryer and disinfection kit of FIG. 1A with a removable desiccant disposed in the container.
Figure 4:
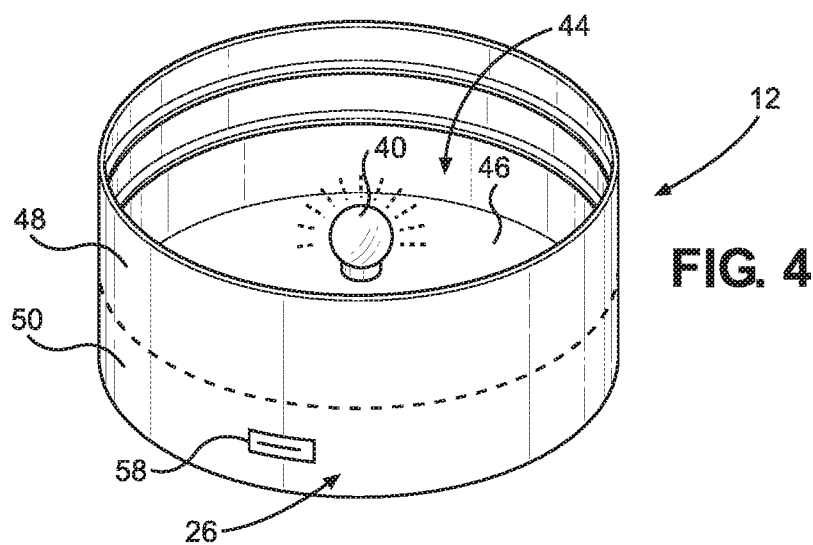
FIG. 4 is a perspective view of an inside portion of the lid for the container of FIG. 3.
Figure 5:
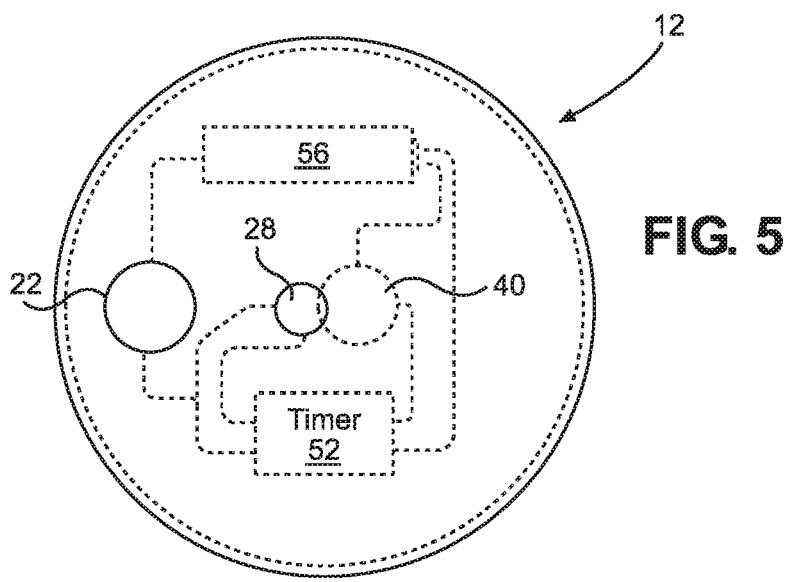
FIG. 5 is a plan view, not to scale, of electrical components within the lid of FIG. 4.
Figure 6:
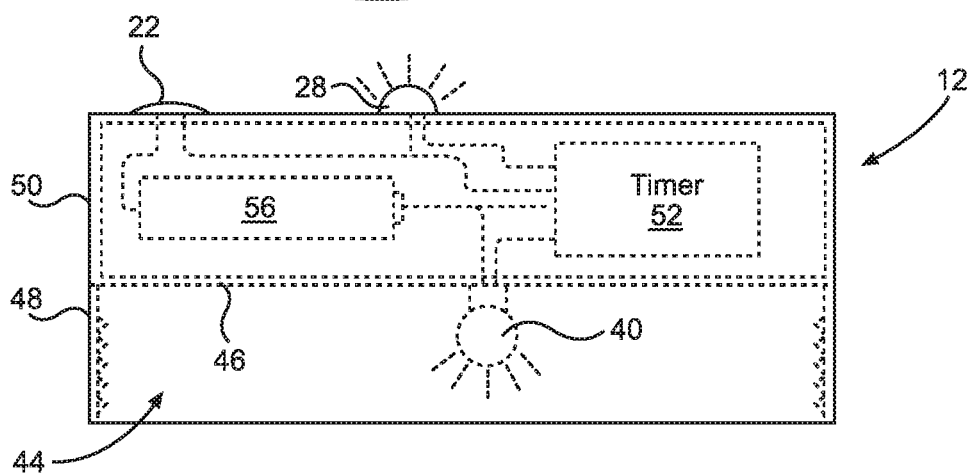
FIG. 6 is an elevational, cross-sectional view of the lid of FIGS. 4 and 5.

FIG. 3 illustrates the desiccant holder 14 disposed in the interior 20 of the container 16. The container 16 has an overall interior size that is suitable for accommodating the desiccant holder 14 and one or more hearing aids 18 therein to be dried and disinfected. In some embodiments, the desiccant may be spherical in shape and disposed in a bottom portion of the container 16 with or without a separate desiccant holder 14. In some embodiments, the container 16 may be a two part container having desiccant disposed in bottom portion of the container and the hearing aids 18 disposed in a top portion of the container wherein the hearing aids 18 are separated from the desiccant by a foraminous separator. In other embodiments, the hearing aids 18 may be disposed in direct contact with the desiccant in the absence of a desiccant holder.

Figure 7:
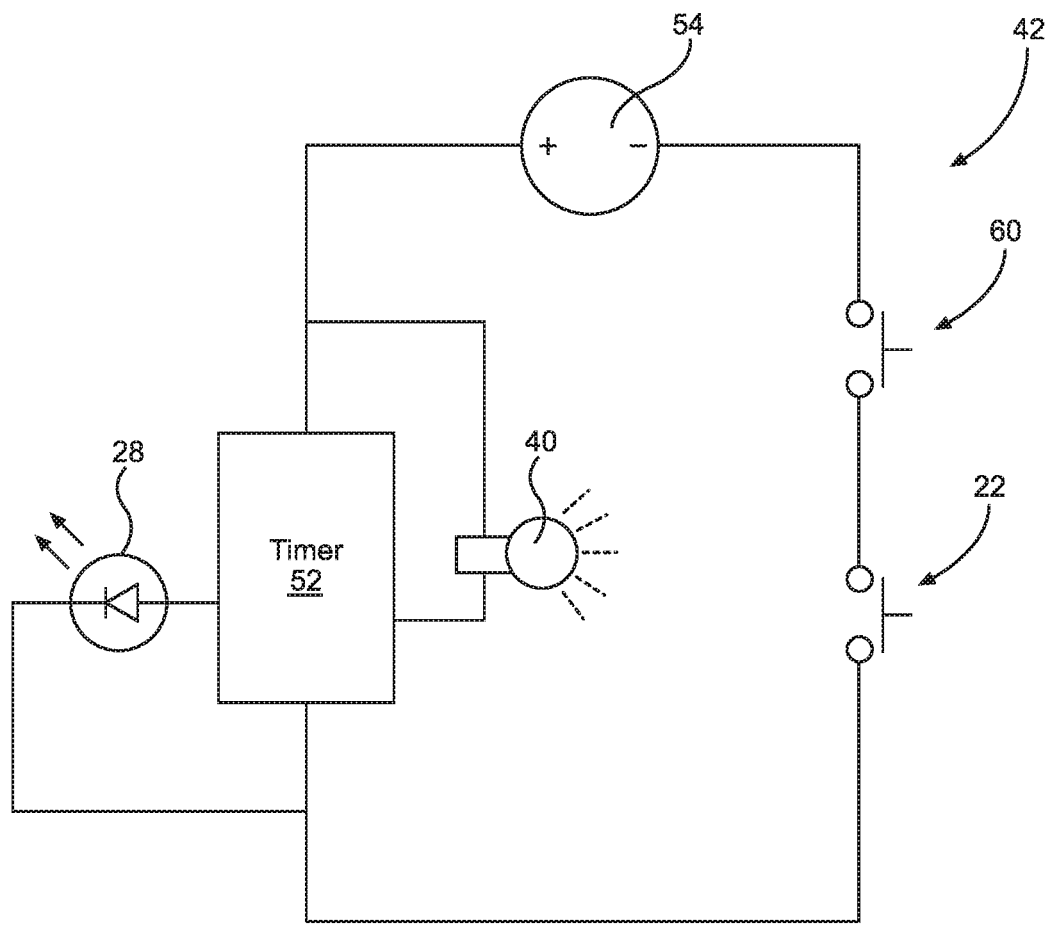
FIG. 7 is a schematic drawing of a control system for the hearing aid dryer and disinfection kit according to FIG. 1A.

An important feature of the hearing aid dryer and disinfection device 10 is the lid 12. Non-limiting aspects of the lid 12 are illustrated in FIGS. 4-7 and include a disinfecting light source, such as an ultraviolet (UV) light source 40, and timer circuitry 42 therefor (FIG. 7). The UV light source 40 is disposed in an interior 44 of the lid 12 on a partition 46 that separates an interior portion 48 of the lid 12 from an electronic housing portion 50 of the lid 12. The UV light source 40 may provide direct irradiation of the hearing aids 18 to kill bacteria or the like on surfaces of the hearing aids 18. Also, ozone may be produced by the UV light source 40 to act as a deodorizer.

A suitable UV light source 40 is a UV-C lamp that is a high intensity 50 mm linear (253.7 nm) germicidal lamp rated at 70 uW/cm$^2$. The wavelength of 253.7 nanometers of the UV-C lamp is proven to inhibit colony formation in microorganisms which may significantly reduce itching and infection of the ear canal. In some embodiments, the disinfecting light source produces violet light in the 400-450 nm range to generate Reactive Oxygen Species (ROS) for killing bacteria.

In some embodiments, the UV light source 40 comprises one or more UV light emitting diodes (LEDs). In a preferred embodiment, multiple UV LEDs are distributed across the bottom surface of the lid 12 to evenly illuminate the interior 20 of the container 16.

The interior portion 48 of the lid 12 and the interior 20 of the container 16 may include a UV reflective coating or may be formed from a UV reflective material, such as e-PTFE (expanded polytetrafluoroethylene).

As set forth above, the indicator lamp 28 on the lid 12 is visible to the user and when illuminated indicates that the UV light source 40 is activated to warn the user not to open the lid 12 of the device 10 while the UV light source 40 is on. In a preferred embodiment, the indicator lamp 28 is a light-emitting diode (LED). The timer circuitry 42 may be activated by pressing the switch 22 which may be a capacitive switch or a micro-contact switch. If a capacitive switch is used, the lid 12 is devoid of any moving parts.

The timer circuitry 42 also includes a digital timer 52 that provides illumination of the UV lamp 40 for a predetermined amount of time. The predetermined amount of time may range from a few minutes to several hours or longer.

A power source 54 (FIG. 7) such as a rechargeable or standard battery 56 may be included in the electronic housing portion 50 of the lid 12 to power the digital timer 52, UV light source 40 and LED lamp 28. In some embodiments, a rechargeable battery is used as the power source 54 which may be charged by removing the battery 56 from the lid 12 or by means of a USB connection 58 disposed on the side portion 26 of the lid 12. In some embodiments, the power source 54 is provided through the USB connection 58 in the absence of an internal battery 56.

Many of the structural components of the device 10, including the lid 12, desiccant holder 14 and the container 16 may be made of a durable plastic material. In some embodiments, the container 16 may be made of glass or ceramic.

As shown in FIG. 7, some embodiments of the device 10 include lid removal detection circuitry 60 to detect that the lid 12 has been removed from the container, in which case the UV light source 40 is deactivated. The detection circuitry 60 may comprise a magnetic switch or metal contacts on the threads of the lid 12 and the container 16 that close the circuit powering the UV light source 40 when lid 12 is screwed down tightly.

The invention has been described in detail with particular reference to preferred embodiments thereof, but it will be understood that variations and modifications will be affected with the spirit and scope of the invention.

What is claimed is:

1. A portable electronic component dryer device comprising:
    a container having an interior portion for receiving one or more electronic components for drying;
    an air-tight removable lid for the container, the removable lid comprising a disinfecting light source, and a power source for providing power to the disinfecting light source, wherein light generated by the disinfecting light source is directed into the interior portion of the container; and
    lid removal detection circuitry that deactivates the disinfecting light source upon removal of the lid from the container.

2. The portable electronic component dryer device of claim 1 wherein the lid removal detection circuitry comprises a magnetic switch or metal contacts on the container and the lid, wherein the magnetic switch or metal contacts close a circuit to provide power to the disinfecting light source when lid is secured to the container.

3. The electronic component dryer device of claim 1, wherein the removable lid further comprises a timer circuit that is isolated from the interior portion of the container, the timer circuit for controlling the disinfecting light source to operate during a predetermined period of time.

4. The electronic component dryer device of claim 1, wherein the removable lid further comprises a switch that is isolated from the interior portion of the container, the switch for activating the disinfecting light source.

5. The electronic component dryer device of claim 4, wherein the switch comprises a capacitive switch.

6. The electronic component dryer device of claim 5, wherein the capacitive switch is on a top portion of the removable lid.

7. The electronic component dryer device of claim 1, wherein the disinfecting light source comprises an ultraviolet light source.

8. The electronic component dryer device of claim 7, wherein the ultraviolet light source comprises one more ultraviolet light emitting diodes or one or more ultraviolet lamps.

9. The electronic component dryer device of claim 1, wherein the container comprises a cylindrical container.

10. The electronic component dryer device of claim 1, wherein the removable lid further comprises a power on/off indicator.

11. The electronic component dryer device of claim 1, further comprising a desiccant disposed in the interior portion of the container.

12. The electronic component dryer device of claim 11, wherein the desiccant comprises a replaceable desiccant holder containing desiccant and having vent holes therein.

* * * * *